United States Patent
Yamashita et al.

(10) Patent No.: US 9,868,666 B2
(45) Date of Patent: Jan. 16, 2018

(54) CEMENT CLINKER PRODUCTION SYSTEM

(71) Applicant: MITSUBISHI MATERIALS CORPORATION, Tokyo (JP)

(72) Inventors: Makio Yamashita, Chichibu-gun (JP); Hisanobu Tanaka, Chichibu-gun (JP); Yukio Tanaka, Tokyo (JP); Katsuhiko Ichihara, Miyako-gun (JP); Kazuo Sakamoto, Chichibu-gun (JP); Kazuo Tabata, Chichibu-gun (JP)

(73) Assignee: MITSUBISHI MATERIALS CORPORATION, Tokyo (JP)

( * ) Notice: Subject to any disclaimer, the term of this patent is extended or adjusted under 35 U.S.C. 154(b) by 162 days.

(21) Appl. No.: 14/367,494

(22) PCT Filed: Dec. 20, 2012

(86) PCT No.: PCT/JP2012/083101
§ 371 (c)(1),
(2) Date: Jun. 20, 2014

(87) PCT Pub. No.: WO2013/099763
PCT Pub. Date: Jul. 4, 2013

(65) Prior Publication Data
US 2015/0246849 A1    Sep. 3, 2015

(30) Foreign Application Priority Data
Dec. 26, 2011 (JP) ................................. 2011-283114

(51) Int. Cl.
*C04B 7/44* (2006.01)
*G01N 23/223* (2006.01)
(Continued)

(52) U.S. Cl.
CPC ............ *C04B 7/4446* (2013.01); *C04B 7/425* (2013.01); *G01N 23/223* (2013.01); *G01N 23/20* (2013.01);
(Continued)

(58) Field of Classification Search
CPC ...... G01N 23/223; G01N 23/20; G01N 33/38; G01N 2223/076; C04B 7/425; C04B 7/4446; C04B 7/361; Y02P 40/121
(Continued)

(56) References Cited

U.S. PATENT DOCUMENTS 5,421,880 A * 6/1995 Young ....................... C04B 7/36
                                                         106/745
5,509,962 A   4/1996 Tang
(Continued)

FOREIGN PATENT DOCUMENTS

CN    1122313 A       5/1996
JP    63-180832 A     7/1988
(Continued)

OTHER PUBLICATIONS

On-Line Quality Control Instrumentation for the Cement Industry, Sylvie Valero, ITECA—France, 2009.*
(Continued)

*Primary Examiner* — Alissa Tompkins
*Assistant Examiner* — John Bargero
(74) *Attorney, Agent, or Firm* — Locke Lord LLP

(57) ABSTRACT

The cement clinker production system includes: a first supplying section configured to supply a sulfur source and a fluorine source of mineralizer; a second supplying device configured to supply clinker raw material; a crusher configured to crush the mixed raw material obtained by mixing the clinker raw material with the fluorine source of the mineralizer; a kiln configured to burn the crushed mixed raw (Continued)

material; an introducing section configured to introduce the sulfur source of the mineralizer to the kiln; a third supplying section configured to supply fuel to the kiln; and a test sample-analyzing system configured to collect each of the mixed raw material before the burning and the clinker after the burning and to measure amounts of the fluorine, main components and free lime depending on the type collected.

6 Claims, 3 Drawing Sheets

(51) Int. Cl.
    *C04B 7/42*       (2006.01)
    *G01N 23/20*    (2006.01)
    *G01N 33/38*    (2006.01)

(52) U.S. Cl.
    CPC ....... *G01N 33/38* (2013.01); *G01N 2223/076* (2013.01); *Y02P 40/121* (2015.11)

(58) Field of Classification Search
    USPC .......................................................... 432/106
    See application file for complete search history.

(56) References Cited

U.S. PATENT DOCUMENTS

| | | | | |
|---|---|---|---|---|
| 5,584,895 | A * | 12/1996 | Seike | C04B 18/06 106/705 |
| 2002/0029726 | A1* | 3/2002 | Kunbargi | C04B 7/32 106/692 |
| 2010/0130806 | A1* | 5/2010 | Sakakibara | A62D 3/36 588/318 |

FOREIGN PATENT DOCUMENTS

| | | |
|---|---|---|
| JP | 03-113327 A | 5/1991 |
| JP | 07-017751 A | 1/1995 |
| JP | 07209215 | 8/1995 |
| JP | 2000-034139 | 2/2000 |
| JP | 2001-130932 | 5/2001 |
| JP | 2003-136036 A | 5/2003 |
| JP | 2006-182638 A | 7/2006 |
| JP | 2006-282455 A | 10/2006 |
| JP | 2011-207752 | 10/2011 |

OTHER PUBLICATIONS

Office Action dated Jun. 30, 2015, issued for the Chinese patent application No. 201280063958.4 and English translation thereof.
San-Ju Lin, "Feasibility Study of Calcium Fluoride Sludge of High Technical Industry as Raw Meal for Cement," National Chiao Tung University, paper for a master degree, published on Jul. 2002, 26 sheets including an English abstract thereof.
Office Action dated Jan. 8, 2016, issued for the Taiwanese patent application No. 101148990 and English translation thereof.
Javed I. Bhatty, "Use of Fluxes and Mineralizers in the Cement Industry: A Survey," Portland Cement Association Research and Development information No. 2045 (1996), pp. 5-25 and information sheets (29 pages in total).
"Sample Preparation Machines Laboratory Automation & Control Systems Air Tube Systems," HERZOG Co., Ltd. Catalog for Sample Preparation Machines and partial translation thereof (7 sheets).
"Automated Quality Control in the Apatite-Staffelite Ore Benefication," HERZOG Application note No. 02, (2012) 3 pages.
Cement Plant Supporting Feature of Circulating Society 12, Cement &Concrete, No. 719, (2007), pp. 4-6, information sheets and partial translation thereof (6 pages in total).
Kenji Suzuki et al., "Raw Meal Mixing Control System for Low Alkali Cement Production Plant," Mitsubishi Heavy Industries Technical Review, vol. 39, No. 4, (2002), pp. 224-227and partial translation thereof.
Japan Cement Association, "Report of the Technical Committee on Cement Chemistry C-7: Study on Chemical Analysis Method for Trace Elements in Cement using x-ray Fluorescence Spectrometric Analysis," (2004), p. 1, information sheet and partial translation thereof (5 sheets in total).
Notification (Information Statement) dated Dec. 17, 2014, issued for 2011-283114 and translation thereof (9 pages in total).
H.F.W. Taylor, "Cement Chemistry" Harcourt Brace Jovanovich, 1990, p. 80, p. 93 and a cover page.
Mitsuhiro Ito, "Another Aspect Desired to Cement Plants—The Function of Environmental Purification—", Powder Science & Engineering, May 1, 2005, vol. 37, No. 5, pp. 53 to 59.
G K Molr et al., "Mineralisers, Modifiers and Activators in the Clinkering Process," 9th International Congress on the Chemistry of Cement, 1992, vol. I, pp. 125 to 152.
Tsugiko Takase et al., "Keiko X-sen Bunseki ni Okeru Glass Bead-ho to Funmatsu Press-ho tono Hikaku Hyoka-Chishitsu Shiryochu no Shuyo 10 Genso to Biryo 18 Genso no Teiryo—", Journal of the Center for Regional Affairs, Fukushima University, Sep. 28, 2007, vol. 19, No. 1, pp. 32 to 47.
International Search Report dated Mar. 19, 2013, issued for PCT/JP2012/083101.
Kazuo Yoshii et al., Multiple Unit Control Equipment for Cement Plant, Hitachi Review, vol. 57, No. 12 (1975), pp. 59-64 (with partial translation).
Office Action dated May 18, 2016, Japanese Patent Application No. 2011-283114.
Bhatty, Javed I., Innovations in Portland cement manufacturing, PCA (Portland Cement Association), pp. 178-183, (2012).
Yellepeddi, Ravi, X-ray instruments and their role in cement chemistry, Advances in Cement Technology (Chemistry, Manufacture and Testing) 2nd edition, pp. 781-791, (2002).
Badanoiu, Alina et al., Evaluation of the effect of some mineral additions on the burnability of raw mix in cement production, U.P.B. Sci. Bull., Series B, vol. 71, p. 35, (2009).
Malata-Chirwa, Charles David, Manufacture and properties of fluoride cement, Iowa State University Graduate Theses and Dissertations, p. 13, (2012).
Engelsen, Christian J., Effect of mineralizers in cement production, SINTEF Report, p. 13, (2007).
Office Action, Opposition, Corresponding Thailand Patent Application No. 1401003646, dated Jul. 27, 2016 (partial English translation).
Wang Lan, "Cement Engineer Handbook", China Building Material Industry Press, 1st Edition, pp. 166-167.
Office Action dated Sep. 19, 2016, for Chinese Patent Application No. 201280063958.4.

* cited by examiner

CEMENT CLINKER PRODUCTION SYSTEM

TECHNICAL FIELD

The present invention relates to a cement clinker production system which is suitable for reducing the quantity of heat in burning and capable of producing high-quality cement.

Priority is claimed on Japanese Patent Application No. 2011-283114, filed on Dec. 26, 2011, the content of which is incorporated herein by reference.

BACKGROUND ART

Most of the heat energy required for cement production is consumed in the clinker burning process. Thus, if the burning temperature of clinker can be lowered, then it will be possible to reduce energy cost significantly and $CO_2$ emission quantity.

Conventionally, clinker of ordinary Portland cement is produced by burning mixed raw material at 1450° C. or higher in a rotary kiln. The following methods have been considered to lower the burning temperature in the clinker burning step:

(a) Increasing the amount of liquid phase during burning by changing the composition of clinker and facilitating clinker to be generated even at a relatively low temperature (Non-Patent Document 1).

(b) Placing a rapid heating furnace at a previous process of a rotary kiln in order to rapidly heat the input raw material to a melt-reaction temperature or higher, and then performing a low-temperature burning at a temperature ranging from 1300 to 1400° C. in the rotary kiln (Patent Document 1).

(c) Since a high temperature is required for generating alite, which is the main mineral of clinker, mixing beforehand a substance which serves as a nucleus of crystal formation of alite into the raw material of clinker (Patent Document 2).

However, with respect to method (a), the decrease in liquidity and decrease in strength of cement due to the change of mineral composition is a concern. Method (b) may cause an increase in the cost due to modification of the production equipment. On the other hand, method (c) is advantageous in that high-quality clinker can be burned at a smaller heat consumption rate than before, however, method (c) requires a substance having a melting point which is higher than the liquid phase generation temperature (1200 to 1300° C.) of cement clinker, serving as a nucleus of crystal formation of alite.

(d) Lowering the burning temperature of clinker by adding flux (mineralizer) such as fluorite (calcium fluoride) to the raw material of clinker has been studied. For example, by adding a fluorine source and sulfur source as mineralizer to produce ordinary Portland cement, the burning temperature can be lowered by about 100° C.

For example, fluorite or waste which contains fluorine as a fluorine source of mineralizer, and anhydrous gypsum or fuel having a high sulfur content as a sulfur source are used. These are crushed by a crusher, and then mixed with clay, coal ash, or various incinerated ash which serves as an aluminum source of clinker to adjust the clinker consumption rate, the resultant mixture is dried by a drier, thereafter, mixed with dry clay, limestone, silicastone, and iron raw material serving as clinker and the raw material ratio is adjusted, and then the resultant mixture is crushed by a mill to be introduced to a burning kiln.

PRIOR ART DOCUMENTS

Patent Documents

Patent Document 1: JP Patent Application, First Publication No. H07-17751
Patent Document 2: JP Patent Application, First Publication No. 2006-182638

Non-Patent Document

Non-Patent Document 1: H. F. W. Taylor: Cement chemistry (1990) p 80, p 93

SUMMARY OF THE INVENTION

Problems to be Solved by the Invention

When mineralizer is added to raw material to burn clinker at a lower temperature, it is necessary to grasp exactly the fluorine amount and the quantity of main component in the mixed raw material, and fluorine amount, sulfur trioxide content and free lime amount in the clinker, in order to produce high-quality cement. As a method for measuring these contents, for example, the following measuring methods corresponding to the component are used.

(e) Chemical composition of cement follows JIS R 5204 2002:2002 "X-ray fluorescence analysis method of cement" or JCAS 1-03 "X-ray fluorescence analysis method of Portland cement".

(f) Fluorine amount in cement follows X-ray fluorescence analysis using powder briquettes, or Cement Association Standard Test Method 1-51: 1981 "Methods for determination of trace components of cement raw materials and cement", alternatively, measurement by heating vaporization absorption ion chromatograph.

(g) Amount of added gypsum or rate of hemihydrate follows thermogravimetry differential thermal analysis (TG-DTA), or measurement by powder X-ray diffraction/Rietveld analysis.

(h) Free lime amount (f. CaO) follows Cement Association Standard Test Method I-01:1997 "Quantification method of free calcium oxide", or measurement by powder X-ray diffraction/Rietveld analysis.

A fluorescent X-ray analyzer and an X-ray diffraction analyzer are used in the measurement method above, and collected samples are melted into beads, or pressed and are subjected to analysis. In such a case, in measuring the fluorine amount, if the sample is melted into beads, then fluorine is diluted or volatilized, and as a result, exact quantification cannot be performed. In addition, in measuring free lime content, if the sample is melted into beads, then clinker minerals are degenerated, and as a result, exact quantification cannot be performed. Therefore, in quantifying the fluorine amount or free lime amount, the samples are not melted into beads, but pressed into pressed samples and the resultant pressed samples are subjected to analysis of mineral components by X-ray diffraction to quantify the free lime amount. In this way, it is necessary to prepare test samples under conditions suitable for elements to be measured respectively, using both X-ray diffraction analysis and fluorescent X-ray analysis, in order to exactly measure the fluorine amount and the free lime amount.

It is an object of the present invention to provide a production system which is capable of producing high-quality cement by conducting both X-ray diffraction analysis and fluorescent X-ray analysis, which are necessary for measuring fluorine amount and free lime amount, and preparing test samples with high efficiency, with respect to the mixed raw material before burning and clinker after burning to measure fluorine amount and free lime amount rapidly and exactly.

Means for Solving the Problem

The present invention relates to a cement production system having the following constitution:

[1] A cement clinker production system, including:
a first supplying section configured to supply a sulfur source and a fluorine source of mineralizer;
a second supplying device configured to supply clinker raw material;
a crusher configured to crush the mixed raw material obtained by mixing the clinker raw material with the fluorine source of the mineralizer;
a kiln configured to burn the crushed mixed raw material;
an introducing section configured to introduce the sulfur source of the mineralizer to the kiln; and
a third supplying section configured to supply fuel to the kiln, wherein
the cement clinker production system further includes a test sample-analyzing system configured to collect each of the mixed raw material before the burning and the clinker after the burning and to measure amounts of the fluorine, main components and free lime depending on the type collected, thereby controlling at least any one of supplying amount of the fluorine source and the sulfur source, the supply amount of the mixed raw material, and the supply amount of the fuel based on the measured amounts by the test sample-analyzing system.

[2] The cement clinker production system according to [1] above, wherein
the test sample-analyzing system includes:
a collecting section configured to collect the mixed raw material before the burning and the clinker after the burning;
a bead maker configured to make the collected samples into beads;
a pressing section configured to press the collected samples;
an X-ray diffraction analyzer; and
a fluorescent X-ray analyzer, wherein
test sample preparation of beads or pressed sample is performed depending on the difference between the mixed raw material before the burning and the clinker after the burning,
the amounts of the fluorine, main components and free lime are measured by the X-ray diffraction analyzer or the fluorescent X-ray analyzer depending on the types of the prepared test sample, and
at least any one of the supply amount of the fluorine source and the sulfur source of the mineralizer, the supply amount of the mixed raw material and the supply amount of the fuel is controlled based on the measured amounts.

[3] The cement clinker production system according to [1] or [2] above, wherein
in the test sample-analyzing system, the amounts of the fluorine and the major components are measured by the fluorescent X-ray analyzer after the preparation to the beads or pressed sample from the mixed raw material before the burning, the amount of the free lime of the clinker is measured by the X-ray diffraction analyzer after the preparation to the pressed sample,
the amounts of the fluorine and main components are measured by the fluorescent X-ray analyzer, and
control signals corresponding to the measured amounts are transmitted to the first supplying section of the fluorine source and the sulfur source of the mineralizer and a supplying section of the mixed raw material, thereby controlling the supply amounts.

[4] The cement clinker production system according to any one of [1] to [3] above, wherein
the test sample-analyzing system includes:
a test sample inlet into which the collected mixed raw material and clinker test sample are carried;
a crusher configured to crush the test sample;
a bead maker configured to make the crushed test sample into beads;
a pressing section configured to press the crushed test sample;
an X-ray diffraction analyzer;
a fluorescent X-ray analyzer;
a test sample removing portion; and
a distributor configured to distribute the test sample via the test sample removing portion, wherein
the test sample inlet, the bead maker to make the crushed test sample into beads, the pressing section to press the crushed test sample, the X-ray diffraction analyzer, the fluorescent X-ray analyzer and the test sample removing portion are arranged circularly,
the distributor is placed at the center of the circular arrangement thereof, and
each of the test sample of the mixed raw material and the clinker test sample is distributed by the distributor with the devices through the distributor depending on the kind of the test sample.

[5] The cement clinker production system according to any one of [1] to [4] above, wherein
the mixed raw material is a feed stock obtained by mixing the fluorine source with the clinker raw material, the clinker raw material being obtained by adding collecting dust to raw material fine powder in which coal ash is mixed.

Effect of the Invention

In the production system of the present invention, each of the fluorine amount and the free lime amount of the mixed raw material before burning and clinker is measured, and a suitable amount of each of the mineralizer and the mixed raw material is supplied, depending on the resultant measured amount, and hence the clinker burning temperature can be lowered, without increasing the coating of the mineralizer in the kiln or the pre-heater, thereby high-quality cement can be produced.

In addition, in the production system of the present invention, it is possible to control the amount of fuel based on the free lime amount contained in the clinker, and it is possible to significantly reduce the thermal energy supply units and fuel cost. Further, it is possible to reduce $CO_2$ emission by reducing the amount of fuel to be used.

In accordance with the production system of the present invention, it is possible to use a sludge which contains calcium fluoride as the fluorine source of the mineralizer, and waste gypsum board or fuel which contains a large amount of sulfur can be used as the sulfur source of the

DESCRIPTION OF EMBODIMENTS

Specifically, the embodiments of the present invention will be explained below.

The production system of the present invention includes a first supplying section configured to supply a sulfur source and a fluorine source of mineralizer, a second supplying section configured to supply a clinker raw material, a crusher configured to crush the mixed raw material obtained by mixing the clinker raw material with the fluorine source of the mineralizer, a kiln for burning the crushed mixed raw material, an introducing section configured to introduce the sulfur source of the mineralizer to the kiln, and a third supplying section configured to supply fuel to the kiln. The cement clinker production system further includes a test sample-analyzing system configured to collect each of the mixed raw material before the burning and the clinker after the burning and to measure amounts of the fluorine, main components and free lime depending on the type collected, thereby controlling at least any one of the supply amount of the fluorine source and the sulfur source, supply amount of the mixed raw material, and supply amount of the fuel based on the measured amounts by the test sample-analyzing system.

For example, in the cement clinker production system of the present invention, the test sample-analyzing system may include: a collecting section configured to collect the mixed raw material before the burning and the clinker after the burning; a bead maker configured to make the collected samples into beads; a pressing section configured to press the collected samples; an X-ray diffraction analyzer; and a fluorescent X-ray analyzer, wherein test sample preparation of beads or pressed sample is performed depending on the difference between the mixed raw material before the burning and the clinker after the burning, the amounts of the fluorine, main components and free lime are measured by the X-ray diffraction analyzer or the fluorescent X-ray analyzer depending on the kinds of the prepared test sample, and at least any one of the supply amount of the fluorine source and the sulfur source of the mineralizer, the supply amount of the mixed raw material and the supply amount of the fuel is controlled based on the measured amounts.

Figure 1:
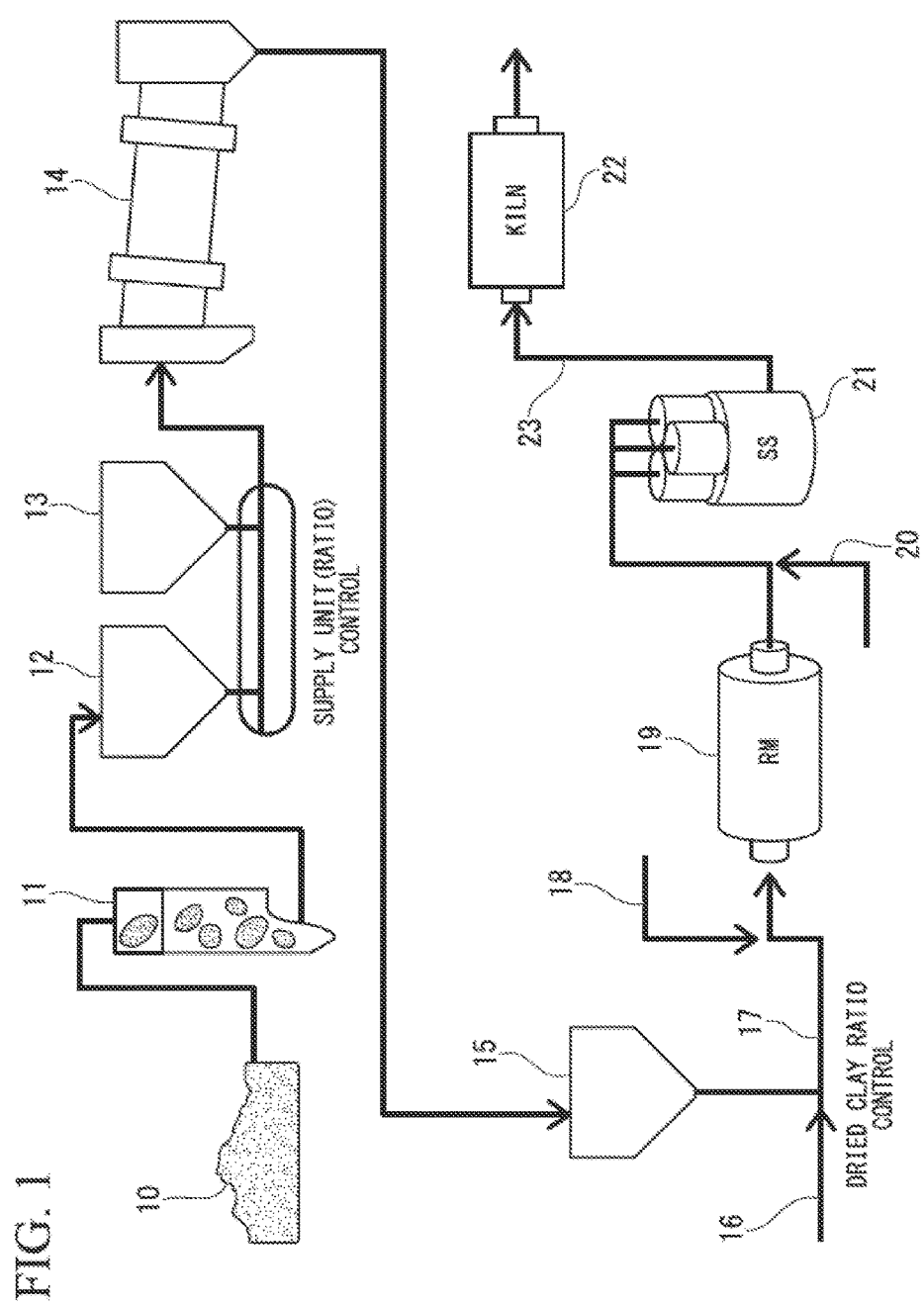
FIG. 1 is a conceptual diagram showing an example of the production system of the present invention.

FIG. 1 shows an example of the production system of the present invention. The production system of the present invention shown in the figure is equipped with a crusher 11 for crushing calcium fluoride sludge 10, which is the fluorine source of the mineralizer, a supplying section 12 for supplying the crushed calcium fluoride sludge, a supplying section 13 for supplying a clay of the clinker raw material, a dryer 14 for drying the mixed raw material of crushed calcium fluoride waste sludge and clay, a supplying section 15 for supplying dry clay to the mixed raw material, a supplying section 17 for supplying the limestone 16 of the clinker raw material, a supplying section 18 for supplying silicastone of clinker raw material and iron raw material, a crusher 19 for crushing these raw materials, a supplying section 20 for supplying coal ash to the crushed raw material, a storing section 21 for storing the mixture of the crushed raw material and coal ash, and an introducing section 23 for introducing mixed raw material (feed stock) which is a mixture of raw material fine powder with collecting dust, the raw material fine powder is mixture of finely crushed raw material with coal ash. It should be noted that a kiln 22 is equipped with a means for introducing waste gypsum board from the kiln outlet part (not shown the drawings).

In addition, the production system shown in FIG. 1 is equipped with a test sample-analyzing system having a means for collecting the mixed raw material before burning (not shown), a means for collecting the clinker after burning (not shown), a crusher for crushing the collected test sample, a bead maker for making the crushed test sample into beads, a pressing section for pressing the crushed test sample, an X-ray analyzer, and a fluorescent X-ray analyzer.

Figure 2:
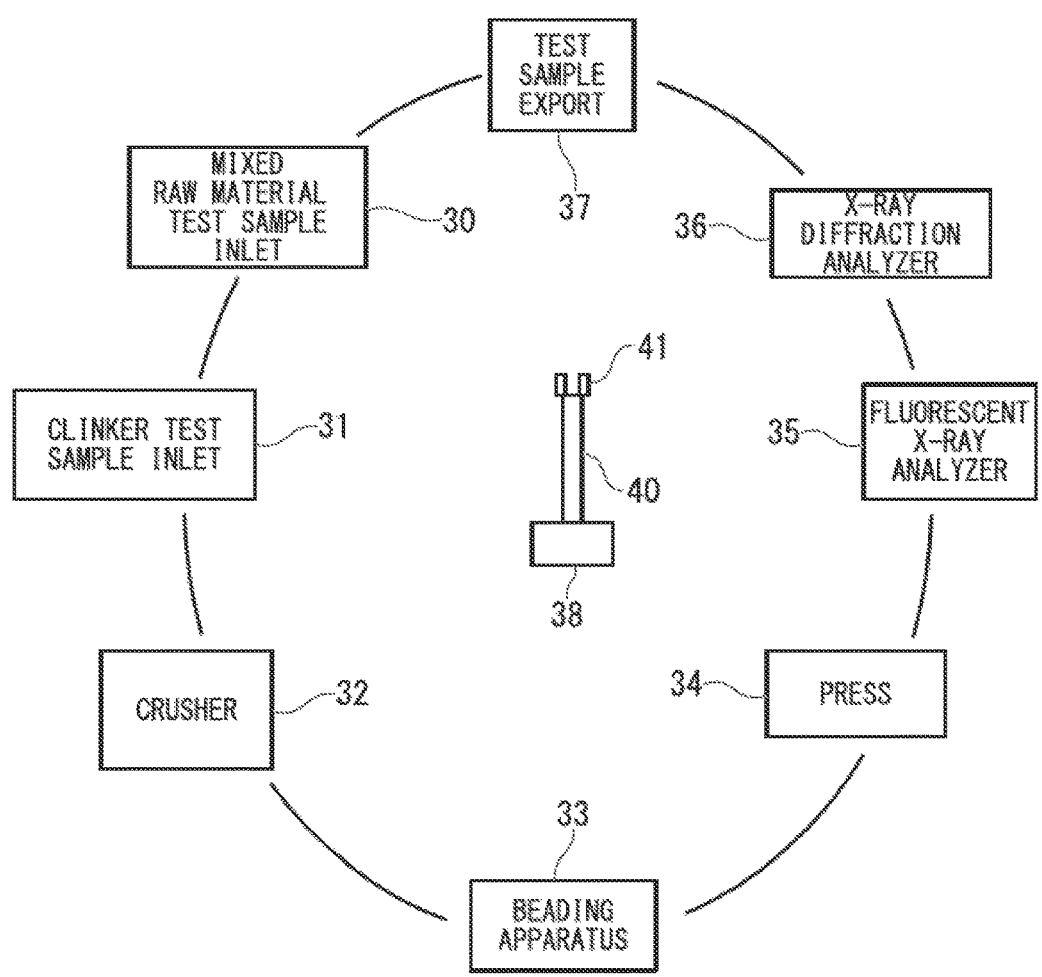
FIG. 2 is a conceptual diagram showing an example of the test sample-analyzing system of the production system of the present invention.

FIG. 2 shows an example of the test sample-analyzing system. In FIG. 2, a test sample inlet 30 into which the collected mixed raw material test sample is carried, a test sample inlet 31 into which the collected clinker test sample is carried, a crusher 32 for crushing these test samples, a bead maker 33 for making the crushed test sample into beads, a press 34 for pressing the crushed test sample, a fluorescent X-ray analyzer 35, an X-ray diffraction analyzer 36, a test sample removing portion 37, and a distributor 38 for taking in and out the test sample with respect to each of the devices are provided.

The test sample inlet 30 and 31, the crusher 32, the beading maker 33, the press 34, the fluorescent X-ray analyzer, the X-ray diffraction analyzer, and the test sample removing portion 37 are circularly arranged. At the center of the circular arrangement, the distributor 38 is displaced. The distributor 38 is equipped with a rotatable arm 40 and a chuck 41 which is installed at the tip of the arm 40.

The test sample carried in the test sample inlet 30 and 31 is held by the chuck 41 of the distributor 38, the arm 40 rotates to input the sample into the crusher 32, thereafter the chuck 41 is opened to leave the test sample and the arm 40 returns to the standby position. After the test sample is crushed into small pieces through the crusher 32, the arm 40 rotates again to the crusher 32, such that the resultant test sample is held by the chuck 41, and the test sample is inputted into the bead maker 33 or the press 34 in the case in which the crushed test sample is the mixed raw material, whereas the test sample is inputted into the press 34 in the case in which the crushed test sample is the clinker test sample. After the test sample is inputted into these devices for test sample preparation, the arm 40 rotates while leaving the test sample to return to the standby position.

After the test sample is prepared into bead test sample or pressed test sample depending on the kind of test sample, the prepared test sample is taken out by the distributor 38, and the arm 40 rotates and carries the prepared test sample to the fluorescent X-ray analyzer 35 or the X-ray diffraction analyzer 36. After being carried, the chuck 41 is opened to leave the prepared test sample at these analyzers, and the arm 40 returns to the standby position.

After the target component is analyzed in the fluorescent X-ray analyzer 35 or the X-ray diffraction analyzer 36, the arm 40 rotates again to hold the test sample, and carries the test sample to the test sample removing portion 37, and the arm 40 returns to the standby position, leaving the test sample. The analyzed test sample is taken out from the test sample removing portion 37.

Figure 3:
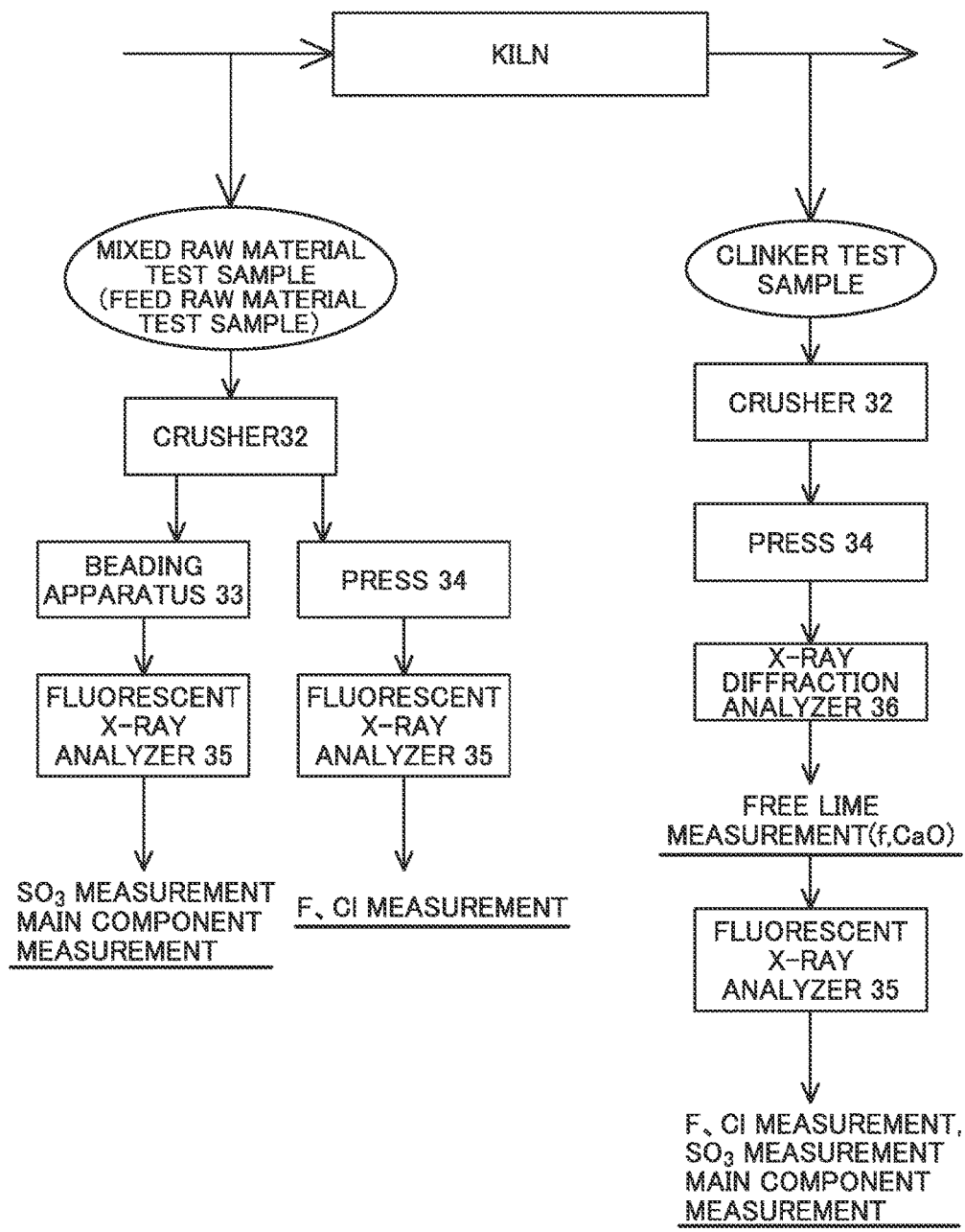
FIG. 3 is a process diagram showing an example of analysis in accordance with the test sample-analyzing system.

An example of the analyzing process of fluorine amount, sulfur trioxide amount, main component amount, and free lime amount using the test sample-analyzing system in the above is shown in FIG. 3. As shown in the figure, the collected mixed raw material before burning is crushed, and then the resultant raw material is prepared into a pressed test sample by which the fluorine amount or chlorine amount is measured. In addition, the crushed test sample is prepared into a bead test sample by which the main component amount and sulfur trioxide amount are measured. Each of the pressed test sample and bead test sample is inputted into the fluorescent X-ray analyzer 35, and subjected to measurement of the fluorine amount, sulfur trioxide amount and main component amount.

On the other hand, the collected clinker test sample is crushed, and then pressed through the press 34 into a pressed test sample. The pressed test sample is inputted into the X-ray diffraction analyzer 36, and is subjected to measurement of mineral composition and free lime content based on the mineral component. Subsequently, the resultant pressed test sample is inputted into the fluorescent X-ray analyzer 35, and is subjected to the measurement of fluorine amount, sulfur trioxide amount, and main component amount.

In this way, according to the test sample-analyzing system above, the collected test sample is prepared into a bead test sample or a pressed test sample, depending on the type of collected test sample and type of element to be measured. Specifically, the mixed raw material before burning is prepared into both a bead test sample and a pressed test sample, and the bead test sample is subjected to measurement of sulfur trioxide amount and main component amount, whereas the pressed test sample is subjected to measurement of fluorine amount. Therefore, a trace amount of fluorine is prepared without diluting and volatilizing, thereby precise quantification can be performed.

In addition, since a clinker test sample is prepared into a pressed test sample and the free lime amount thereof is directly measured thereon, the clinker mineral does not degenerate, thereby the free lime amount and the mineral composition can be precisely measured. In addition, the resultant pressed test sample can be used to measure the fluorine amount, sulfur trioxide amount, and main component amount.

In the test sample-analyzing system, a series of operations from taking the test sample in and out to exporting after analysis can be continuously performed by an automatic controlling circuit. It should be noted that each of the sulfur trioxide amount, fluorine amount and main component amount can be measured in accordance with the fluorescent X-ray analysis method (bead method or powder briquette method), whereas the free lime amount (f. CaO) can be measured in accordance with the calibration curve method, the internal standard method, or Rietveld analysis method using powder X-ray diffraction.

Each of control signals depending on the measured fluorine amount, sulfur trioxide amount and main component amount is transmitted to each of the sections for supplying the fluorine source and the sulfur source of the mineralizer, the section for supplying the mixed raw material, and the section for supplying fuel, thereby each of the supply amounts is controlled.

With respect to the production system of the present invention, the above-mentioned example is one which collects the mixed raw material before burning to analyze; however, it is also possible to collect each of the clinker raw material and the raw material fine powder of the mixed raw material individually, and to measure the fluorine amount, the sulfur trioxide amount and the main component amount. The production system of the present invention involves such modes.

INDUSTRIAL APPLICABILITY

According to the production system of the present invention, each of the fluorine amount and free lime amount of the mixed raw material before burning and the clinker is measured, and an appropriate amount of mineralizer and the mixed raw material is supplied, depending on the measured amount, and hence the clinker burning temperature can be lowered, without increasing the coating due to the mineralizer in the kiln and the pre-heater, thereby it is applicable to the production of high-quality cement.

DESCRIPTION OF REFERENCE NUMBERS

10 Calcium Fluoride Sludge
11 Crusher
12, 13 Supplying Section (Hopper)
14 Dryer
15 Supplying Section (Hopper)
16 Limestone
17 Supplying Section
18 Supplying Section
19 Crusher (RM)
20 Supplying Section
21 Storing Section
22 Kiln
23 Introducing Section
30, 31 Test Sample inlet
32 Crusher
33 Bead Maker
34 Press
35 Fluorescent X-Ray Analyzer
36 X-Ray Diffraction Analyzer
37 Test Sample Removing Portion
38 Distributor
40 Arm
41 Chuck

The invention claimed is:

1. A cement clinker production system, comprising:
a first supplying section configured to supply a fluorine source of mineralizer and a clinker raw material;
a mixing section configured to mix the supplied clinker raw material with the supplied fluorine source of the mineralizer to obtain the mixed raw material;
a crushing section configured to crush the mixed raw material; and
an introducing section configured to introduce a sulfur source of the mineralizer, fuel and the crushed mix raw material to the kiln to produce a clinker by burning the crushed mix raw material,
wherein
the cement clinker production system further comprises a test sample-analyzing system,
the test sample-analyzing system comprising:
a collecting section configured to collect each of the mixed raw material before the burning and the clinker after the burning;

a bead section configured to make the collected mixed raw materials into a beads mixed raw material test sample;

a first pressing section configured to make the collected mixed raw materials into a pressed mixed raw material test sample;

a second pressing section configured to make the collected clinker into a pressed clinker test sample;

a first measurement section configured to measure the amount of the fluorine of the mixed raw material from the pressed mixed raw material test sample;

a second measurement section configured to measure the amounts of the sulfur trioxide and main components of the mixed raw material from the beads mixed raw material test sample; and a third measurement section configured to measure the amounts of the sulfur trioxide, the fluorine, main components and free lime of the clinker from the pressed clinker test sample, thereby controlling at least any one of the supply amount of the fluorine source and the sulfur source, the supply amount of the mixed raw material, and the supply amount of the fuel based on the measured amounts by the test sample-analyzing system.

2. The cement clinker production system according to claim 1, wherein the test sample-analyzing system comprises:

an X-ray diffraction analyzer; and a fluorescent X-ray analyzer, wherein the amounts of the sulfur trioxide, the fluorine and the main components of the mixed raw material and the clinker, and the amount of the free lime of the clinker are measured by the X-ray diffraction analyzer or the fluorescent X-ray analyzer, and at least any one of the supply amount of the fluorine source and the sulfur source of the mineralizer, the supply amount of the mixed raw material and the supply amount of the fuel is controlled based on the measured amounts.

3. The cement clinker production system according to claim 1, wherein in the test sample-analyzing system, amounts of the sulfur trioxide, the fluorine and the main components are measured by the fluorescent X-ray analyzer after the preparation to the beads or pressed sample from the mixed raw material before the burning, the amount of the free lime of the clinker is measured by the X-ray diffraction analyzer after the preparation to the pressed sample, the amounts of the fluorine and the main components are measured by the fluorescent X-ray analyzer, and control signals corresponding to the measured amounts are transmitted to the first supplying section of the fluorine source and the sulfur source of the mineralizer and a supplying section of the mixed raw material, thereby controlling the supply amounts.

4. The cement clinker production system according to claim 1, wherein the test sample-analyzing system comprises:

a test sample inlet into which the collected mixed raw material and clinker test sample are carried;

a crusher configured to crush the test sample;

a bead maker configured to make the crushed test sample into beads;

a pressing section configured to press the crushed test sample;

an X-ray diffraction analyzer;

a fluorescent X-ray analyzer;

a test sample removing portion; and a distributor configured to distribute the test sample via the test sample removing portion, wherein the test sample inlet, the bead maker to make the crushed test sample into beads, the pressing section to press the crushed test sample, the X-ray diffraction analyzer, the fluorescent X-ray analyzer and the test sample removing portion are arranged circularly, the distributor is placed at the center of the circular arrangement thereof, and each of the test sample of the mixed raw material and the clinker test sample is distributed by the distributor with the devices through the distributor depending on the type of test sample.

5. The cement clinker production system according to claim 1, wherein the mixed raw material is a feed stock obtained by mixing the fluorine source with the clinker raw material, the clinker raw material being obtained by adding collecting dust to raw material fine powder in which coal ash is mixed.

6. The cement clinker production system according to claim 2, wherein in quantifying the fluorine amount or free lime amount, the samples are pressed into pressed samples and the resultant pressed samples are subjected to analysis of mineral components by X-ray diffraction to quantify the fluorine amount or the free lime amount.

* * * * *